United States Patent [19]

Harris et al.

[11] 4,240,982
[45] Dec. 23, 1980

[54] NOVEL ONIUM SURFACTANTS

[75] Inventors: Robert F. Harris, Midland, Mich.; Earl H. Wagener, Concord, Calif.

[73] Assignee: The Dow Chemical Company, Midland, Mich.

[21] Appl. No.: 43,868

[22] Filed: May 29, 1979

Related U.S. Application Data

[62] Division of Ser. No. 895,558, Apr. 12, 1978, which is a division of Ser. No. 416,308, Nov. 15, 1973, Pat. No. 4,093,663.

[51] Int. Cl.$^3$ .................. C07C 91/26; C07C 91/38
[52] U.S. Cl. .................. 564/285; 260/501.18; 260/501.19; 564/287
[58] Field of Search .................. 260/567.6 M, 501.18, 260/501.19

[56] References Cited

U.S. PATENT DOCUMENTS

| | | | |
|---|---|---|---|
| 2,824,861 | 2/1958 | Conbere et al. | 260/567.6 M |
| 2,876,263 | 3/1959 | Mark | 260/567.6 M |
| 2,897,170 | 7/1959 | Gruber et al. | 260/567.6 M |
| 3,102,912 | 9/1963 | Nevacher et al. | 260/567.6 M |
| 3,155,591 | 11/1964 | Hilfer | 260/567.6 M |
| 3,879,464 | 4/1975 | Kalopissis et al. | 260/567.6 M |
| 4,009,255 | 2/1977 | Kalopissis et al. | 260/567.6 M |

*Primary Examiner*—James H. Reamer
*Attorney, Agent, or Firm*—Michael L. Glenn

[57] ABSTRACT

Novel onium surfactants are described which correspond to the formula $X[(CH_2CH_2O)_mCH_2-R-CHR'-Q^\oplus A^\ominus]_n$, wherein X is an n-valent hydrophobic radical derived by the removal of n-atoms of active hydrogen from an organic compound; m is one or more; R is a divalent aromatic hydrocarbon radical of from 6 to about 14 carbon atoms, the chain-length of which may be interrupted by oxygen or sulfur atoms; R' is hydrogen or methyl and is methyl only when R is m- or p-phenylene; $Q^\oplus$ is a quaternized atom of nitrogen or phosphorus or a tertiary atom of sulfur; $A^\ominus$ is a compatible anion; and n is from 1 to 5. The following compound is an example $C_9H_{19}-C_6H_4-O(CH_2CH_2O)_{15}CH_2-C_6H_4-CH_2-S^\oplus(CH_3)_2Cl^\ominus$. The novel surfactants are prepared in two steps. In step 1, various nonionic surfactants are reacted with certain chloromethylated aromatics in the presence of a strong base to give novel intermediates which are subsequently reacted in step 2 with tertiary amines, pyridines, tertiary phosphines, sulfides, thiourea etc. to give the onium surfactants.

13 Claims, No Drawings

NOVEL ONIUM SURFACTANTS

CROSS REFERENCE TO RELATED APPLICATION

This is a division, of aplication Ser. No. 895,558 filed 4/12/78 which is a division of application Ser. No. 416,308, filed 11/15/73 (now U.S. Pat. No. 4,093,663).

BACKGROUND OF THE INVENTION

This invention pertains to novel onium surfactants and the precursors thereof.

Surface active agents (surfactants) have been defined as any compound that reduces surface tension when dissolved in water or water solutions, or which reduces interfacial tension between two liquids, or between a liquid and a solid. See "The Condensed Chemical Dictionary," Eighth Edition by G. G. Hawley, Van Nostrand Reinhold Co., N.Y. (1971). Surfactants are useful as detergents, wetting agents and/or emulsifiers and are normally described as being either ionic (cationic or anionic) or nonionic surfactants. The nonionic surfactants are of particular interest in the instant invention.

The nonionic surfactants form a known class of compounds having many members. Those having an end block(s) of polyoxyethylene units terminated with a hydroxyl group (i.e. $-(CH_2CH_2O)_m H$) are particularly useful commercially. Such compounds are normally prepared by condensing ethylene oxide (EO) onto a hydrophobic (lyophilic) compound bearing at least one active hydrogen. By "active hydrogen" is meant hydrogen active in the Zerewitinoff reaction. E.g. hydrogen on a carboxyl group, a phenolic hydroxyl group, a mercaptan group, etc. are active hydrogens). The nonionic surfactants are also characterized by their hydrophiliclyophilic balance (HLB).

The concept of HLB is now widely accepted, particularly for the nonionic surfactants, and is fully described in the literature. See, for example, the text "Emulsions—Theory and Practice," 2nd Ed., A.C.S. Monograph No. 162, by Paul Becher, Reinhold Publishing Corp., N.Y. (1965), pp. 232-255.

A wide variety of nonionic surfactants are described in "McCutcheon's Detergents and Emulsifiers—1972 Annual," published by McCutcheon's Division, Allured Publishing Corp., N.J. (1972) and in "Nonionic Surfactants," Vol. 1 of the "Surfactant Science Series," edited by M. J. Schiek, published by Marcel Dekker, Inc., N.Y. (1967).

The known class of nonionic surfactants whose members have from 1 to 5 end blocks of polyoxyethylene units terminated with hydroxyl and having an HLB of from 1 to about 30 (preferably from about 5 to about 18) are used herein as reactants leading to the novel onium surfactants. This class of nonionic surfactants is represented by the formula $$X + (CH_2CH_2O)_m H]_n, \quad I$$

wherein X is an n-valent hydrophobic radical derived by the removal of n-atoms of active hydrogen from an organic compound, m is an integer of at least 1 and is normally from 1 to about 200 and is most frequently from 4 to about 50; and n is an integer of from 1 to 5. The reactants having from 1 to 3 end blocks of polyoxyethylene units (i.e. n is 1, 2 or 3) are currently preferred and those having only one (n is 1) end block of polyoxyethylene units are most preferred. The latter compounds are referred to as monofunctional nonionic surfactants.

SUMMARY OF THE INVENTION

A novel class of onium surfactants, and precursors thereof, has now been discovered.

The novel onium surfactants are represented by the formula

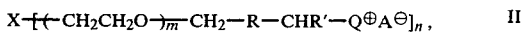  II wherein X, m and n have the aforesaid meaning; R is a divalent aromatic hydrocarbon radical of from 6 to about 14 carbon atoms (preferably 6 to 12 carbon atoms), the chain-length of which can be interrupted by oxygen or sulfur atoms; R' is hydrogen or methyl and is methyl only when R is m- or p-phenylene, $Q^\oplus$ is a quaternized atom of nitrogen or phosphorus or a tertiary atom of sulfur; and $A^\ominus$ is a compatible anion.

The novel precursors are represented by the formula $X + (CH_2CH_2O)_m CH_2 - R - CHR' - Cl]_n$, wherein X, R, R', m and n have the aforesaid meaning. The precursors are likewise surfactants.

DETAILED DESCRIPTION OF THE INVENTION

The Precursors

The precursors are prepared by reacting nonionic surfactants with bis-chloromethylated aromatics in the presence of a strong base.

Suitable nonionic surfactants leading to the precursor are described above and include: ethoxylated aliphatic alcohols and mercaptans, such as the ethoxylated derivatives of decanol, dodecanol, hexadecanol, octadecanol, duodecanol, oleyl alcohol, butylbenzyl alcohol, nonylphenethyl alcohol, etc.; ethoxylated alkylphenols, such as the ethoxylated derivatives of butylphenol, hexylphenol, octylphenol, dodecylphenol, octadecylphenol, and the corresponding mercaptans and the like; polyoxyethylene esters and amides of carboxylic acids and carboxamides, such as the esters derived by reacting ethylene oxide with decanoic, dodecanoic, pentadecanoic, octadecanoic, cis-9-octadecenoic, cis,cis-9,12-octadecadienoic, cis,cis,cis-9,12,15-octadecatrienoic, hexylbenzoic and octylphthalic acid and the ethoxylated derivatives of the corresponding carboxamides, and the like; and the polyoxyethylene-capped polymers of propylene oxide and/or butylene oxide, such as the polyoxyethylene capped polymers of propylene oxide and/or butylene oxide initiated with methanol, ethanol, propanol, butanol or other alkanol, ethylene glycol, propylene glycol, butylene glycol, glycerol, pentaerythritol, sorbitan, sorbitol, sucrose, etc.; and other like compounds. See pages 205-221 of the 1972 Annual of "McCutcheon's Detergents and Emulsifiers" handbook for other examples included within the class of suitable nonionic surfactants for use herein. The ethoxylated derivatives of linear primary alkanols or alkenols, linear alkanoic or alkenoic acids, and alkylphenols having from about 12 to about 24 carbon atoms are preferred along with the polyoxyethylene-capped polymers of propylene oxide and/or butylene oxide initiated with a $C_1$ to $C_4$ alkanol, ethylene glycol, propylene glycol, butylene glycol or glycerol. The ethoxylated derivatives of alkylphenols having from about 12 to about 24 carbon atoms are the most preferred nonionic surfactants for use herein.

The bis-chloromethylated aromatic reactants are likewise a known class of compounds. They are represented by the formula $ClCH_2-R-CHR'Cl$, wherein R and R' are as defined above. Examples of suitable such compounds include 1-chloromethyl-3-(α-chloroethyl)benzene, 1-chloromethyl-4-(α-chloroethyl)benzene and the bis-chloromethyl derivatives of benzene, naphthalene, anthracene, phenanthrene, diphenyl oxide, diphenyl sulfide, toluene, xylene, methylnapthalene, and the like. There are known techniques for preparing such compounds (for example, by reacting the aromatic compounds with chloromethyl methyl ether, or by reacting the bis-methylated aromatic compound with chlorine, etc.). The preferred compounds are bis-chloromethylated derivatives of benzene, naphthalene, diphenyl oxide or diphenyl sulfide. The most preferred compounds are m- and p-bis-(chloromethyl)-benzene.

The stoichiometry of the reaction requires one mole of bis-chloromethylated reactant per hydroxy equivalent weight of nonionic surfactant (i.e. the mole weight of the surfactant divided by the number of terminal hydroxyethyleneoxy groups on the surfactant molecule). Best results are achieved by using an excess of the bis-chloromethylated aromatic reactant. This excess reduces the amount of undesirable by-product produced in the reaction (e.g. bis-ethers, etc.).

The reaction between the nonionic surfactants and the bis-chloromethylated aromatics is conducted in the presence of a strong base. Suitable bases include alkali metals (e.g. sodium, potassium), alkali metal alkoxides (e.g. sodium or potassium methoxide, ethoxide, t-butoxide, etc.) and the like. The base reacts with the HCl formed in the course of the reaction and tends to both catalyze the reaction and drive it to completion. The amount of base used can be varied but optimum results seem to be attained when the base is present in slight excess of 1 equivalent of base per hydroxy equivalent weight of nonionic surfactant.

The reaction is normally conducted with stirring at ambient conditions of temperature and pressure for periods of from a few minutes up to a few days. Elevated temperatures will, of course, increase the reaction rate and reaction temperatures of up to about 80° C. have been used with success on combinations of reactants having a low rate of reactivity.

We have found it convenient to conduct the reaction by adding the bis-chloromethylated aromatic reactant to a mixture of the nonionic surfactant and base. A liquid reaction medium may be used, if desired, to facilitate temperature control and contact between the reactants. Any inert solvent can be used and we have found t-butanol to be particularly useful in this regard.

Precursors corresponding to the general formula given above in which R' is methyl can be prepared in an analogous but alternative procedure. Namely, m- or p-vinyl-benzyl chloride can be reacted with the nonionic surfactant to give a vinylbenzyl ether of the surfactant which in turn is reacted with HCl to give the desired product.

The Onium Surfactants

The novel onium surfactants are conveniently prepared by reacting the precursors with an appropriate nitrogen, phosphorus or sulfur-containing organic compound (e.g. a tertiary amine, a pyridine, a thiourea, a tertiary phosphine, a sulfide, etc.). Normally this reaction is conducted in an inert liquid reaction medium (e.g. water or water/lower alkanol mixtures) and the onium product is recovered therefrom by conventional techniques. Ambient conditions of temperature and pressure are normally satisfactory but elevated temperatures (e.g. up to about 80° C.) can be used advantageously in some instances. The course (extent) of the reaction can be easily followed by the production of ionic chloride.

The nitrogen and phosphorus containing organic compounds which can be used in preparing the onium surfactants have at least one reactive tertiary amino or phosphorus atom in the molecule which is quaternized. Suitable such amines therefore include those corresponding to the formulas $R_1R_2R_3N$ and $R_1R_2R_3P$, wherein $R_1$, $R_2$ and $R_3$ are hydrocarbon radicals, or inertly-substituted hydrocarbon radicals, having a combined total carbon content of up to about 30 carbon atoms. Alternatively, the nitrogen atom may be a member of a heterocyclic ring. Examples of suitable such amines and tertiary phosphines include those having the following $R_1$, $R_2$ and $R_3$ values:

TABLE 1

| $R_1$ | $R_2$ | $R_3$ |
|---|---|---|
| $CH_3$ | $CH_3$ | $CH_3$ |
| $C_2H_5$ | $C_2H_5$ | $C_2H_5$ |
| $C_4H_9$ | $C_4H_9$ | $C_4H_9$ |
| $C_{10}H_{21}$ | $C_{10}H_{21}$ | $C_{10}H_{21}$ |
| $CH_3$ | $CH_3$ | $C_{12}H_{25}$ |
| $C_2H_5$ | $C_2H_5$ | $C_{10}H_{21}$ |
| $CH_3$ | $CH_3$ | $C_6H_5CH_2$ |
| $C_2H_5$ | $C_4H_9$ | $C_6H_5CH_2CH_2$ |
| $CH_3$ | $C_6H_5CH_2$ | $C_6H_5CH_2$ |
| $CH_3$ | $CH_3$ | $C_6H_5$ |
| $C_6H_5$ | $C_6H_5$ | $C_6H_5$ |
| $CH_3$ | $CH_3$ | cyclohexyl |
| $C_4H_9$ | $C_4H_9$ | $CH_2CH=CH_2$ |
| $C_2H_5$ | $C_2H_5$ | $C_{10}H_{20}$ |
| $CH_3$ | $CH_3$ | $CH_3C_6H_4CH_2$ |
| $C_2H_5$ | $C_2H_5$ | $C_4H_9C_6H_4CH_2$ | and other like compounds. Examples of suitable heterocyclic amines include N-methylpyrrole, pyridine, quinuclidine, triethylenediamine, and the like. The preferred amines are pyridine and trialkylamines having a total carbon content of from 3 to about 18 carbon atoms. The preferred tertiary phosphines are triphenylphosphine and trialkylphosphines having a total carbon content of from 3 to about 18 carbon atoms (particularly tri-n-butylphosphine).

The sulfur-containing organic compounds which can be used in preparing the onium surfactants have at least one reactive sulfur atom in the molecule which is converted to a sulfonium species in the reaction. Suitable such compounds include those corresponding to the formula $R_4SR_5$, wherein $R_4$ and $R_5$ are hydrocarbon radicals or inertly-substituted hydrocarbon radicals having a combined total carbon content of from 2 to about 24 carbon atoms. Alternatively, $R_4$ and $R_5$ can be joined to form a 5- or 6-membered heterocyclic ring. Examples of suitable such compounds include those having the following $R_4$ and $R_5$ values:

TABLE 2

| $R_4$ | $R_5$ |
|---|---|
| $CH_3$ | $CH_3$ |
| $C_2H_5$ | $C_2H_5$ |
| $C_2H_4OH$ | $C_2H_4OH$ |
| $C_6H_{13}$ | $C_6H_{13}$ |
| $CH_3$ | $C_{10}H_{21}$ |

TABLE 2-continued

| R$_4$ | R$_5$ |
|---|---|
| CH$_3$ | C$_{18}$H$_{37}$ |
| CH$_3$ | C$_6$H$_5$CH$_2$ |
| C$_4$H$_9$ | C$_6$H$_5$CH$_2$CH$_2$ |
| CH$_3$ | C$_8$H$_{16}$—C$_6$H$_4$CH$_2$ |
| CH$_3$ | C$_6$H$_5$ |
| cyclohexyl | CH$_2$CH=CH$_2$ |
| CH$_3$ | C$_4$H$_8$—C$_6$H$_4$— | and other like compounds. Examples of suitable heterocyclic sulfur compounds include thiophene, tetrahydrothiophene, thiaoxane, pentamethylene sulfide, and the like. The preferred compounds are tetrahydrothiophene and dialkylsulfides having a total carbon content of from 2 to about 18 carbon atoms and having methyl, ethyl or hydroxyethyl as at least one of the two alkyl substituents.

Other suitable amino and sulfur-containing compounds include thioureas which correspond to the following formula:

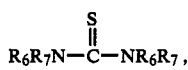

wherein R$_6$ and R$_7$ are hydrogen or lower alkyl (C$_1$ to C$_4$). Examples of which include thiourea and the N,N'-dimethyl, N,N'-dibutyl, N,N,N',N'-tetramethyl derivatives of thiourea, and the like. Of this class, thiourea is the preferred species.

As used above, the term "inertly-substituted hydrocarbon radical" is meant to define hydrocarbon radicals bearing one or more substituents which are inert in the process of preparing the onium surfactants. Examples of such inert substituents include hydroxyl, thiol, halo, cyano, and the like.

The following examples will further illustrate the invention:

thereafter (aliquots 1, 2 and 3, respectively). The amount of ionic chloride (milliequivalents, meq.) in each aliquot was determined and is reported below:

TABLE 3

| Aliquot | meq. Cl$^\ominus$/gm. | Conversion (%)* |
|---|---|---|
| 1 | 0.127 | 58 |
| 2 | 0.199 | 91 |
| 3 | 0.210 | 96 |

*Premised on amount of sodium consumed.

After a total of 4 hours at about 40° C., the mixture was filtered to remove the solids from the liquid product. The filter cake was washed with 2 liters of benzene and the liquid wash combined with the original filtrate. The benzene and t-butanol solvents were removed under reduced pressure at an elevated temperature (ca. 80° C. at 5 mm. Hg.) leaving the liquid product and unreacted 1,4-bis(chloromethyl)benzene. The latter compound was removed by warming the mixture at 170°–180° C. at 1 mm. Hg. thereby leaving the desired product as a light yellow oil (382.4 g.). Hydroxyl titration and the nuclear magnetic resonance (nmr) spectrum of this material indicated that it contained 5.7 weight percent of unreacted ethoxylated nonylphenol, 6.6 weight percent of the adduct of 2 moles of ethoxylated nonylphenol and 1 mole of 1,4-bis(chloromethyl)benzene and 87.7 weight percent of the desired product, total weight basis in each instance. This represents a 78.8 percent product yield, based on ethoxylated nonylphenol added. A 0.1 weight percent aqueous solution of the product had a surface tension of 32.8 dynes/cm. at 25° C. The product is therefore a surfactant.

EXAMPLES 2–11

The compounds in Table 4 were prepared following substantially the procedure detailed in Example 1 and by using the appropriate reactants.

TABLE 4

| Ex. | Product | Yield (%) | Surface Tension |
|---|---|---|---|
| 2 | p-C$_9$H$_{19}$C$_6$H$_4$O$\left(CH_2CH_2O\right)_4$CH$_2$—C$_6$H$_4$—CH$_2$Cl | 93 | 39.2 |
| 3 | p-C$_9$H$_{19}$C$_6$H$_4$O$\left(CH_2CH_2O\right)_9$CH$_2$—C$_6$H$_4$—CH$_2$Cl | 86 | 31.6 |
| 4 | p-C$_9$H$_{19}$C$_6$H$_4$O$\left(CH_2CH_2O\right)_{20}$CH$_2$—C$_6$H$_4$—CH$_2$Cl | 65 | 37.8 |
| 5 | p-C$_9$H$_{19}$C$_6$H$_4$O$\left(CH_2CH_2O\right)_{30}$CH$_2$—C$_6$H$_4$—CH$_2$Cl | 94 | 36.9 |
| 6 | p-C$_9$H$_{19}$C$_6$H$_4$O$\left(CH_2CH_2O\right)_{80}$CH$_2$—C$_6$H$_4$—CH$_2$Cl | 100 | 39.8 |
| 7 | p-C$_9$H$_{19}$C$_6$H$_4$O$\left(CH_2CH_2O\right)_{15}$CH$_2$—C$_6$H$_4$—O—C$_6$H$_4$—CH$_2$Cl | 95 | 34.5 |
| 8 | C$_2$H$_5$O$\left(\underset{CH_3}{CH}-CH_2O\right)_{9.7}\left(CH_2CH_2O\right)_7$CH$_2$—C$_6$H$_4$—CH$_2$Cl | 88 | 36.2 |
| 9 | n-C$_{12}$H$_{25}$O$\left(CH_2CH_2O\right)_4$CH$_2$—C$_6$H$_4$—CH$_2$Cl | 94 | 28.8 |
| 10 | CH$_3$(CH$_2$)$_{10}$CH$_2$S$\left(CH_2CH_2O\right)_{15}$CH$_2$—C$_6$H$_4$—CH$_2$Cl | 96 | 33.7 |
| 11 | CH$_3$(CH$_2$)$_{10}$CH$_2$OCH$_2$—C$_6$H$_4$—CH$_2$Cl | 94 | 30.3 |

EXAMPLE 1 Preparation of
C$_9$H$_{19}$C$_6$H$_4$O$(-$CH$_2$CH$_2$—O$)_{15}$CH$_2$C$_6$H$_4$CH$_2$Cl An ethoxylated p-nonylphenol corresponding to the formula p-C$_9$H$_{19}$C$_6$H$_4$O$(-$CH$_2$CH$_2$O$)_{15}$H (342 g., 0.4 mole) and t-butanol (3 liters) and metallic sodium (13.8 g., 0.6 mole) were charged under a nitrogen atmosphere to a 5 liter, 3 necked flask equipped with a mechanical stirrer, thermometer and condenser. The mixture was warmed at gentle reflux with stirring until all of the sodium had reacted.
The temperature of the mixture was then brought to 40° C. and 1,4-bis(chloromethyl)benzene (350 g., 2.0 mole) was added in one shot with stirring. The temperature exothermed less than 2° C. Aliquots of the mixture were taken immediately after the addition of the 1,4-bis(-chloromethyl)-benzene and at periods of 2 and 4 hours In some instances, the processes were conducted at 60° C. and it was noted that the reaction was nearly instantaneous at that temperature. In all of the above examples, the products were viscous liquids or wax-like solids.

EXAMPLE 12

The product of Example 3 was also prepared as follows: Metallic sodium (2.3 g., 0.10 mol) and t-butanol (400 ml.) were charged under a nitrogen blanket to a 1 liter, 3 necked flask equipped with a mechanical stirrer, thermometer, condenser and dropping funnel. After the reaction between the sodium and butanol was complete, the ethoxylated nonylphenol (88.1 g., 0.10 mol) was added and the temperature raised to 60° C. To this was added dropwise a solution of 1,4-bis(chloromethyl)benzene (17.5 g., 0.10 mol) dissolved in 100 ml. benzene. The resultant slurry was maintained at 60° C. for 2 hours. The sodium chloride produced was removed by filtration and the solvent was stripped away under reduced pressure leaving the crude product as a straw-colored viscous liquid (96 g., 94 percent yield).

EXAMPLE 13

Following the above general procedure, the compound

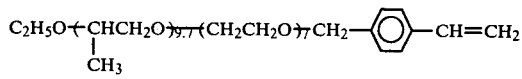

$C_2H_5O{+}CHCH_2O{\}_{m\text{-}7}(CH_2CH_2O{\}_7)CH_2-\phi-CH=CH_2$
|
$CH_3$ was prepared by adding a stoichiometric amount of p-vinyl-benzyl chloride (VBC) dropwise with stirring over a 1 hour period to

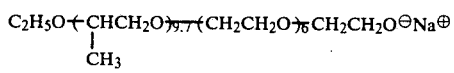

$C_2H_5O{+}CHCH_2O{\}_{m\text{-}7}(CH_2CH_2O{\}_{76})CH_2CH_2O^{\ominus}Na^{\oplus}$
|
$CH_3$ in t-butanol at 50° C. The reaction proceeded in about 97 percent conversion of reactants 5 hours after the addition of VBC. The t-butanol solvent was stripped off under reduced pressure leaving the product as a viscous liquid.

The above product (50 g.) was then charged along with an equal weight of methanol to a reaction vessel equipped with a condensor, thermometer, mechanical stirrer, caustic scrubber and a gas sparger tube. Anhydrous gaseous HCl (55.5 g.) was then added to the solution at a constant rate over a 4 hour period. The volatiles were stripped off under reduced pressure leaving the product as a light yellow liquid weighing 49.8 g. (approximately 93 percent yield) and corresponding to the formula

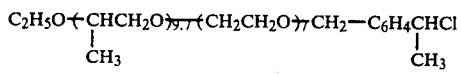

$C_2H_5O{+}CHCH_2O{\}_{m\text{-}7}(CH_2CH_2O{\}_7)CH_2-C_6H_4CHCl$
|  |
$CH_3$  $CH_3$ Other derivatives were similarly prepared by reacting VBC with various nonionic (surfactants in the presence of base) and subsequent reaction with HCl.

Other procedures for preparing the above precursors will be readily apparent to those skilled in the art.

PREPARATION OF THE ONIUM SURFACTANTS

EXAMPLE 14 Preparation of
p-$C_9H_{19}C_6H_4O{+}CH_2CH_2O{\}_{15}CH_2-C_6H_4-CH_2-S^{\oplus}{+}CH_3{\}_2Cl^{\ominus}$ A portion of the product from Example 1 (90 g., 0.088 mol) was mixed with methanol (170 ml), water (30 ml) and dimethyl sulfide (37 ml., 0.5 mol) in a sealed vessel equipped with a mechanical stirring means. The reaction mixture was stirred at ambient temperature for several hours and the progress of the reaction measured by titration of ionic chloride in aliquots removed from the mixture. After 46 hours the conversion of the reactant to the corresponding sulfonium chloride seemed to level off at about 85 percent conversion. Water (300 ml.) was added to the mixture and any unreacted dimethyl sulfide was removed along with methanol and some water by subjecting the mixture to a reduced pressure at ambient temperature. The desired sulfonium chloride was thus obtained as a yellow aqueous solution containing 34 weight percent sulfonium chloride solids. The surface tension of a 0.1 weight percent aqueous solution of this sulfonium surfactant was 36.3 dynes/cm. at 25° C.

Using essentially the same procedure, other onium surfactants were prepared by reacting the precursors from Examples 1-11 with triphenylphosphine, dimethyl sulfide, pyridine, thiourea or triethylamine in a water/(m)ethanol medium for periods of up to about 80 hours at ambient temperature. The work-up of the products was essentially the same as above. The onium surfactants were all obtained as aqueous solutions which, when diluted with water to a 0.1 weight percent concentration, had surface tensions of about 43 dynes/cm. at 25° C. or less (mostly in the range of 30–40 dynes/cm.). These onium surfactants corresponded to the formulas in Tables 5 to 11.

TABLE 5

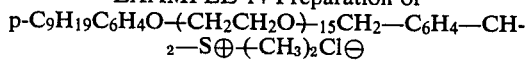

$R-O{+}CH_2CH_2O{\}_m-CH_2-\phi-CH_2-S^{\oplus}(CH_3)_2Cl^{\ominus}$

| Ex. | R | m | Surface Tension (dynes/cm.) |
|---|---|---|---|
| 14 | $C_9H_{19}C_6H_4$ | 15 | 36.3 |
| 15 | $C_9H_{19}C_6H_4$ | 4 | 30.7 |
| 16 | $C_9H_{19}C_6H_4$ | 7 | 36.9 |
| 17 | $C_9H_{19}C_6H_4$ | 9 | 33.9 |
| 18 | $C_9H_{19}C_6H_4$ | 20 | 38.8 |
| 19 | $C_9H_{19}C_6H_4$ | 80 | 41.8 |
| 20 | $C_{11}H_{23}$ to $C_{15}H_{31}$ mixture | 12 | 32.5 |
| 21 | n-$C_{12}H_{25}SCH_2CH_2$ | 14 | 44.0 |
| 22 | $C_2H_5O{+}CH-CH_2O{\}_{m\text{-}7}$<br>\|<br>$CH_3$ | 7 | — |

TABLE 6

$C_9H_{19}-\phi-O{+}CH_2CH_2O{\}_{15}-CH_2-\phi-CH_2-S^{\oplus}(CH_3)_2Cl^{\ominus}$

| Ex. | Position Isomer | Surface Tension (dynes/cm) |
|---|---|---|
| 23 | ortho | 38.3 |
| 24 | meta | 36.7 |
| 25 | para | 36.3 |

TABLE 7

$C_9H_{19}-\phi-O(CH_2CH_2O)_mCH_2-\phi-CH_2SC\overset{\overset{\oplus}{NH_2}}{\underset{NH_2}{}}\quad Cl^{\ominus}$

| Ex. | m | Surface Tension (dynes/cm) |
|---|---|---|
| 26 | 9 | 37.8 |
| 27 | 15 | 37.6 |
| 28 | 40 | 40.7 |

TABLE 8

$C_9H_{19}-\phi-O(CH_2CH_2O)_mCH_2-\phi-CH_2\overset{\oplus}{N}(CH_2CH_3)_3Cl^{\ominus}$

| Ex. | m | Surface Tension (dynes/cm.) |
|---|---|---|
| 29 | 4 | 35.2 |
| 30 | 7 | 36.6 |
| 31 | 9 | 38.2 |
| 32 | 15 | 39.2 |
| 33 | 20 | 37.9 |
| 34 | 40 | 41.7 |

TABLE 9

R—O(CH₂CH₂O)ₘCH₂—⟨C₆H₄⟩—CH₂N⊕⟨C₅H₅⟩ Cl⊖

| Ex. | R | m | Surface Tension (Dynes/cm) |
|---|---|---|---|
| 35 | $C_9H_{19}C_6H_4$ | 4 | 35.7 |
| 36 | $C_9H_{19}C_6H_4$ | 7 | 36.6 |
| 37 | $C_9H_{19}C_6H_4$ | 15 | 35.5 |
| 38 | $C_9H_{19}C_6H_4$ | 20 | 38.6 |
| 39 | $C_{11}H_{23}$ to $C_{15}H_{31}$ mixture | 12 | |
| 40 | $C_2H_5O$(CHCH₂O)$_{9.7}$—CH₃ | 7 | |

TABLE 10

$C_9H_{19}$—⟨C₆H₄⟩—O(CH₂CH₂)₇OCH₂—⟨C₆H₄⟩—CH₂P⊕(C₆H₅)₃ Cl⊖

| Ex. | Surface Tension (dynes/cm) |
|---|---|
| 41 | 39.9 |

TABLE 11

R—O—(CH₂CH₂O)ₘCH₂—⟨C₆H₄⟩—CHN⊕—CH₃ Cl⊖

| Ex. | R | m |
|---|---|---|
| 42 | $C_9H_{19}C_6H_4$ | 15 |
| 43 | $C_2H_5O$(CHCH₂O)$_{9.7}$—CH₃ | 7 |

Other oniums can be similarly prepared by reacting the precursors with other tertiary amines (e.g. trimethylamine, benzyldimethylamine, etc.), with other sulfides (e.g. dipropyl sulfide, dibutyl sulfide, dodecyl methyl sulfide, benzyl methyl sulfide, diphenyl sulfide, thiophene, tetrahydrothiophene, etc.), with other thioureas (e.g. N,N,N',N'-tetramethyl (or tetraethyl) thiourea, etc.) with phosphines (e.g. tri-n-butylphosphine, trioctylphosphine, etc.), and the like.

We claim:

1. An onium surfactant corresponding to the formula X{(CH₂CH₂O)ₘCH₂-R-CHR'-Q⊕A⊖}ₙ, wherein X is the hydrophobic portion of a n-valent radical derived by the removal of n-atoms of active hydrogen from an organic compound, said organic compound being a nonionic surfactant having a hydrophilic-lipophilic-balance of from 1 to about 30 and having the structural formula X{(CH₂CH₂O)ₘH}ₙ; m is an integer of at least 1 and is the same in each of the above formulae; R is a divalent aromatic hydrocarbon radical of from 6 to about 14 carbon atoms, the chain length of which can be interrupted by oxygen or sulfur atoms; R' is hydrogen or methyl and is methyl only when R is m- or p-phenylene; Q⊕ is a quaternary ammonium radical corresponding to the formula —NR₂R₃R₃, wherein R₂, R₃ and R₄ are each independently hydrocarbon radicals or inertly-substituted hydrocarbon radicals and wherein the total number of carbon atoms in R₂, R₃ and R₄ does not exceed 30; A⊖ is a compatible anion; and n is an integer of from 1 to 5 and is the same in each of the above formulae.

2. The surfactant defined in claim 1 wherein n is an integer of from 1 to 3.

3. The surfactant defined in claim 1 wherein n is 1.

4. The surfactant defined by claim 1 wherein R is m- or p-phenylene or a divalent radical of diphenyl oxide or diphenyl sulfide.

5. The surfactant defined by claim 1 wherein R is m- or p-phenylene.

6. The surfactant defined by claim 1 wherein m is an integer of from 1 to about 200.

7. The surfactant defined in claim 6 wherein m is an integer of from 4 to about 50.

8. The surfactant defined by claim 1 wherein X is the hydrophobic portion of a n-valent radical, said radical being derived by removal of active hydrogen from an ethoxylated aliphatic alcohol, phenol, organic carboxylic acid or carboxamide, or a polyoxyethylene-capped polymer of propylene oxide and/or butylene oxide.

9. The surfactant defined by claim 8 wherein said radical is derived by the removal of active hydrogen from ethoxylated alkanols, alkenols, alkylphenols, alkanoic acids or amides of alkanoic acids of from about 10 to about 24 carbon atoms or polyoxyethylene-capped polymers of propylene oxide and/or butylene oxide.

10. The surfactant defined by claim 9 wherein said radical is derived by the removal of active hydrogen from an ethoxylated alkylphenol.

11. The surfactant defined by claim 10 wherein said ethoxylated alkylphenol is an ethoxylated nonylphenol.

12. The surfactant defined by claim 11 wherein m is an integer of from 1 to about 200, R is a divalent radical of benzene; A⊖ is halide, nitrate, sulfate, bisulfate, methylsulfate, lower alkanoate, benzoate, or tosylate, and n is 1.

13. The surfactant defined by claim 12 wherein Q⊕ is —NR₂R₃R₄ wherein R₂–R₄ are alkyl and the total aggregate carbon content of R₂, R₃ and R₄ is up to about 24 carbon atoms.

* * * * *